United States Patent [19]

Elissando et al.

[11] Patent Number: 4,617,409

[45] Date of Patent: Oct. 14, 1986

[54] AMINOMETHYLTRIORGANOTIN COMPOUNDS, PREFERABLY α-MONO OR DISUBSTITUTED; AND THE METHOD OF PREPARATION

[75] Inventors: Bernard Elissando; Michel Pereyre, both of Talence; Jean-Paul Quintard, Gradignan, all of France

[73] Assignee: Centre National de la Recherche Scientifique, France

[21] Appl. No.: 626,158

[22] Filed: Jun. 29, 1984

[51] Int. Cl.$^4$ .............................................. C07F 7/22
[52] U.S. Cl. .......................................... 556/87; 546/2; 549/206
[58] Field of Search .................. 260/429.7; 549/206; 546/2; 556/87

[56] References Cited

U.S. PATENT DOCUMENTS

| | | | |
|---|---|---|---|
| 3,723,089 | 3/1973 | Peterson | 260/429.7 X |
| 4,472,429 | 9/1984 | Drabek | 260/429.7 X |
| 4,504,488 | 3/1985 | Davis | 260/429.7 X |

OTHER PUBLICATIONS

Abel et al., J. Organometallic Chem. 97, 159–165 (1975).
Lequan et al., J. Organometallic Chem. 113, C13–C16 (1976).
Peterson et al., J. Organometallic Chem. 66, 209–217 (1974).
Peterson, J. Organometallic Chem. 21, p63–p64 (1970).
Peterson et al., JACS 93(16), pp. 4027–4031 (1971).

*Primary Examiner*—Helen M. S. Sneed
*Attorney, Agent, or Firm*—Steinberg & Raskin

[57] ABSTRACT

The invention concerns a method of preparation of aminomethyltriorganotin compounds, preferably α-mono or disubstituted, the new tin compounds obtained thereby and an application of said tin compounds to the synthesis of aminomethylorganometallic compounds and to the regiospecific preparation of β-aminoalcohols. The intermediate tin and metallic compounds are new. The method for preparing the tin compounds comprises reacting an iminium salt with a corresponding stannylanion, preferably a triorganostannylanion. This method provides best yields and provides regiospecific β-aminoalcohols useful by having in most cases a large spectrum of pharmacological activities.

14 Claims, No Drawings

AMINOMETHYLTRIORGANOTIN COMPOUNDS, PREFERABLY α-MONO OR DISUBSTITUTED; AND THE METHOD OF PREPARATION

BACKGROUND OF THE INVENTION

The present invention essentially relates to a method of preparation of aminomethyltriorganotin compounds, preferably α-mono or disubstituted; new aminomethyltriorganotin compounds α-mono or disubstituted; the application of said aminomethyltriorganotin compounds to the synthesis of aminomethyltriorganotin compounds, preferably α-mono or disubstituted; new aminomethylorganometallic compounds α-mono or disubstituted and the application of said aminomethyltriorganotin compounds or of said aminomethylorganometallic compounds to the regiospecific preparation of β-aminoalcohols.

Hitherto only non-substituted aminomethyltrialkyltin compounds of the formula $R_3SnCH_2N<$ have been synthesized and described in R. G. KOSTYANOVSKII, A. K. PROKOF'EV, Izv. Akad. Nauk. SSSR. Ser. Khim., (1965). 175; E. W. ABEL, R. J. ROWLEY, J. Organometal. Chem., 97, (1975), 159. The method of preparation involved the use of halogenomethyltrialkyltins and of secondary amines or salts thereof. This method is considered to be of little interest due to the difficulty of preparation of the organostannic reactants (see D. SEYFERTH, S. B. ANDREWS, R. L. LAMBERT, J. Organometal. Chem., 37. (1972), 69; D. SEYFERTH, E. G. ROCHOW, J. Am. Chem. Soc., 77, (1955), 1302).

Another method has been described in the literature by D. J. PETERSON in "D. J. PETERSON, J. Organometal. Chem., 21, (1970), P 63; D. J. PETERSON, J. Am. Chem. Soc., 93, (1971), 4027; D. J. PETERSON, J. F. WARD, J. Organometal. Chem., 66, (1974), 209." This method comprises reacting a tri-n-butyl stannyllithium with electrophilic substrates consisting essentially of α-amino thio ethers and only gives access to aminomethyltributyltin compounds not substituted.

Further, this method is difficult to carry out and is of little interest since it lacks the presence of a substituent on the methyl part thereof.

And, it is and becomes of high interest to be in a position to synthesize aminomethyltriorganotin compounds which will be mono- or disubstituted in α position since the aminomethyltrialkyltin compounds are important to prepare, through transmetallation with the aid of an organometal, preferably an organolithium, the corresponding aminomethyl organometallic compounds which constitute reactants of high potentiality in synthesis, practically inaccessible through other ways (see A. KRIEF, Tetrahedon, 36, (1980), 2531).

The corresponding chemical reaction is the following.

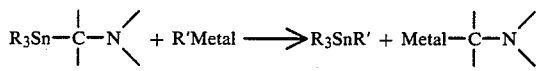

SUMMARY OF THE INVENTION

One essential object of the present invention is therefore to provide a new method of preparation of aminomethyltriorganotin compounds, preferably α-mono or disubstituted which is easy to be put into practice and which needs only readily available reactants, while providing a high yield in reaction compound.

Another essential object of the present invention is to provide new aminomethyltriorganotin compounds α-mono or disubstituted, in particular as intermediate compounds for the synthesis of corresponding organometal compounds, preferably organolithium compounds.

Accordingly, a further object of the present invention is an application of the aminomethyltriorganotin compounds to the synthesis of a new aminomethylorganometallic compound, preferably α-mono or disubstituted. A further object of the present invention is the provision of new aminomethylorganometallic compounds α-mono or disubstituted.

Again, a further object of the present invention is an application of the abovesaid aminomethyltriorganotin compounds or of said aminomethylorganometallic compounds to the preparation of regiospecific β-aminoalcohols which constitute compounds of high potentiality notably in the pharmaceutical field.

All these objects are achieved by the present invention.

Accordingly, the present invention provides a method of preparation of aminomethyltriorganotin compounds, preferably α-mono or disubstituted, characterized in that it comprises reacting an iminium salt with a corresponding stannyl anion, preferably a triorganostannyl anion.

According to a specific embodiment of the invention method, the iminium salt is preferably an iminium halide, having the following chemical formula:

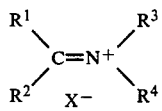

Wherein $R^1$, $R^2$ each independently can represent hydrogen; $R^1$, $R^2$, $R^3$, $R^4$ each independently can represent any organic radical saturated or unsaturated, aliphatic or alicyclic, preferably having from 1 to 20 carbon atoms, more preferably from 1 to 12 carbon atoms and most preferably from 1 to 8 carbon atoms. The preferred organic radicals are an alkyl, cycloalkyl, aryl, phenyl, benzyl, furyl group and two R groups taken together can form a ring saturated or even unsaturated;

X is a halogen atom, preferably selected from a chlorine atom, iodine atom or bromine atom, and most preferably is a chlorine atom.

The reaction is advantageously performed within a solvent in particular ethers, hydrocarbons or mixtures of solvents, but most preferably in ethers. Diethylethers, tetrahydrofuran, dimethoxyethane and other ethers can be used but diethylether is the most preferable ether.

According to a preferred embodiment, the stannyl anion is a triorgano-stannyl anion of formula $R_3SnM$ with M representing MgCl,Li, Na and K is preferably MgCl; R is any organic radical as in the case of the iminium salts, R is preferably an alkyl group and most preferably n-butyl; X is preferably a halogen atom and most preferably a chlorine ion.

According to specific embodiments the iminium salt is selected from:

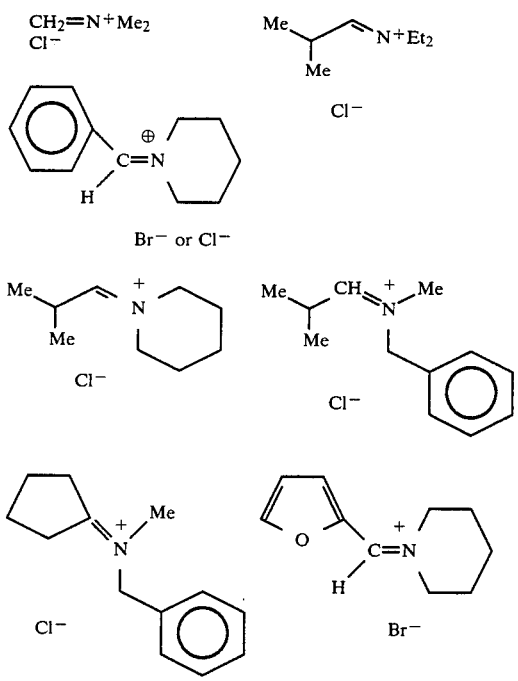

Summarizing the above, the invention method of preparation of the aminomethyltriorganotin compounds, preferably α-mono or disubstituted can be represented by the following chemical reaction:

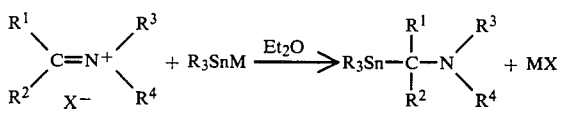

The aminomethyltriorganotin compounds which are mono or disubstituted in position α are new compounds which form a part of the present invention. Those compounds are preferably represented by the following chemical formula I:

wherein each of the R radicals or substituents is as previously defined with the proviso that at least one of $R^1$, $R^2$ is other than hydrogen.

The present invention also concerns an application of the above defined aminomethyltriorganotin compounds, preferably α-mono or disubstituted to the preparation of corresponding α-amino organometallic compounds by reacting an organometal with said aminomethyltriorganotin compounds according to the following chemical reaction:

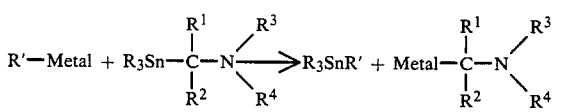

With the R radicals being as previously defined; R' being independently as defined for the R radicals, R' being preferably identical to R; the metal is preferably selected from Li+, K+, Na+, Mg+, Al+ <; most preferably the metal is Li+.

The present invention also concerns the new amino methyl organometallic compounds α-mono or disubstituted which are preferably of the following chemical formula II:

Wherein each of the R radicals is as previously defined with the proviso that at least one of $R^1$, $R^2$ is other than hydrogen, the metal is as previously defined and is preferably lithium.

It must be noted that in the above set forth chemical reaction for preparing the new aminomethylorganometallic compounds, one of the reaction products is constituted by a tin tetra substituted compound which is easily recycled to constitute the starting organometallic reactant for forming the stannylanion.

Further, according to the present invention, the most prefered stannylanion is constituted by tri-n-butyl-stannylmagnesiumchloride which is easily obtained as described in "J. C. LAHOURNERE, J. VALADE, C. R. Acad. Sci, Ser. C., 270, (1970), 2080."

Further, the starting iminium reactants are also easily available and preparable as described in "Iminium Salts in Organic Chemistry", H. Böhme, H. G. Viehe Eds, Advances in Organic Chemistry, vol. 9, part. 1 and 2, (1976).

DESCRIPTION OF THE PREFERRED EMBODIMENTS

The invention new organometallic compounds are very useful intermediate compounds for the synthesis of a number of very useful organic compounds.

One of the most preferred applications of the invention aminomethyltin or metallic compounds which are preferably α-mono or disubstituted is the regiospecific synthesis of β-amino alcohols.

According to this most preferred application, the method is characterized in that it comprises reacting at first the previously defined aminomethyltin compound onto an organometallic compound and reacting the thereby obtained aminomethylorganometallic compound with a ketone or an aldehyde of Formula

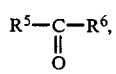

which both reactions can be summarized by the following chemical reaction:

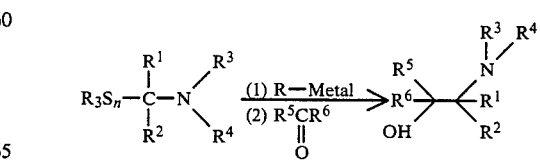

Wherein each of $R^5$, $R^6$ can be hydrogen or one is H and the other is an organic radical or both $R^5$ and $R^6$ are an organic radical, as defined for the other $R^1$ to $R^4$, the metal is as above defined.

It is of prime importance to note that this invention method provides regiospecific β-amino alcohols which are very useful notably since they have in most cases a large spectrum of pharmacological activities. Some examples of such compounds synthesized according to the invention method will be set forth in the following description.

In this respect, it must be outlined that the hitherto known method for synthesizing β-amino alcohols were often based on the addition of the amine onto an epoxide according to the following reaction:

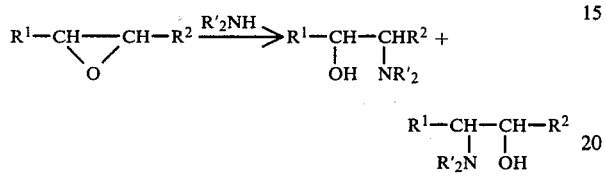

not permitting to control the regioselectivity of the reaction. The amino group is indeed fixed preferentially to the side the less hindered of the epoxide so that mixtures of regioisomers are obtained when the hinderings are close at the location of the two epoxidic carbons.

For this type of reaction including addition of an amine onto an epoxide, see E. J. COREY, et. al, J. Am. Chem. Soc., 87, 1 353 (1965) and P. A. CROOKS, R. SZYNDLER, Chem. and Ind. 1 111, (1973); J. H. POSNER, D. Z. ROGERS, J. Am. Chem. Soc. 99, 8208 (1977); L. E. OVERMAN, L. A. FLIPPIN, Tetrahedron Letters 22, 195 (1981).

Other methods only reach aminoalcohols of the type HO-C-$CH_2NH_2$ (see the W. E. PARHAM, C. S. ROOSEVELT, Tetrahedron Letters 923, (1971); R. F. MEYER et. al. J. Med. Chem. 16, 1 113 (1973); D. A. EVANS et. al. J. Org. Chem. 39, 914 (1974); T. KAUFFMANN, H. BERG, E. KÖPPELMANN, D. KUHLMANN Chem. Ber. 110, 2 659 (1977); or aminoalcohols of the type R-C-H and the substituents $NH_2$ CH-$CH_2OH$ (see M. L. ANHOURY et. al. J. Chem. Soc. PERKIN Trans. I, 191, (1974); and G. BARLUENGA, F. FANANAS, M. YUS J. Org. Chem. 44, 4 798 (1979).

But according to these last methods, there is no problem of regioselectivity which latter problem is put forward only when it is wished to synthesize β-aminoalcohols which are substituted both onto the carbon bearing the hydroxyl and onto the carbon bearing the nitrogen.

SHARPLESS has tried to solve this problem through aminohydroxylation of alkenes (SHARPLESS, et. al. J. Am. Chem. Soc. 97, 2 305 (1975); J. Org. Chem. 41, 177 (1976) ).

SEEBACH has proposed a method reaching amino alcohols with secondary or primary amine functions through the denitrosation of hydroxynitrosamines in D. SEEBACH and D. ENDERS, Angew, Chem. Int. Ed; 14, 15 (1975).

This way is dangerous in that the nitrosamines used have carcinogenic properties and this needs a one pot reaction in view of lowering the risks of contamination.

In view of the above, it is clear that the present invention provides a new and unobvious way of preparing regiospecific β-aminoalcohols according to a very simple method providing great yields in reaction products whereas said reaction products are easily separated one from the other.

Other characterizing features, advantages will appear from the following description given by way of nonlimitative examples. In all examples, the percentages are given by weight unless otherwise stated.

EXAMPLE 1

Preparation of iminium chlorides

A number of methods for preparing iminium salts is known from "Iminium Salts in Organic Chemistry", H. BÖHME, H. J. VIEHE Editions, Advances in Organic Chemistry, Volume 9, Part 1 and 2, (1976).

The simplest iminium salt of Formula $CH_2=N^+(CH_3)_2$, $X^-$ is known as Eschenmoser salt and is commercially available.

The inventors have prepared the iminium salts by treating at $-80°$ C. the corresponding enamines as taught by PETERSON in J. Am. Chem. Soc. 79, 1 115 (1957) by a hydrochloric anhydrous solution within ether (approximately 3N). The enamines were themselves prepared according to the method of UMEN and HOUSE, organic synthesis, 53, 48 (1973), or OPITZ et. al. Liebig Ann., 649, 36 and 47 (1961), or using BEWZING Angew. Chem., 71, 521 (1959) or even according to DULOV Bull. Soc. Chim. Fr., 967 (1960). The yield is practically quantitative in the iminium salts.

EXAMPLE 2

Preparation of the α-amino alkyl tri-n-butyltin compounds

According to the invention method, the α-amino alkyltributyltin compounds are obtained as above said through simple chemical reaction for instance and preferably between the tributylstannyl magnesium chloride and the corresponding imminium halogen salt which is preferably a chloride salt.

Here-below is given a specific example of preparation of a dimethylaminomethyltributyltin compound which is the simplest α-aminoalkyltributyltin compound, the processing conditions remaining identical for the preparation of any other α-aminoalkyltributyltin compound.

Within a trineck glass flask of 250 ml, previously dried, are introduced 35.38 grams of tributyltin hydride (0.125 mole) to which is slowly added dropwise one equivalent of an etherified solution of isopropylmagnesium chloride (about 1N).

This reaction which is exothermic, produces a gaseous evolvement of propane. After complete addition, said reaction medium which is milky white, is brought to reflux with the aid of a lamp (about 100 watts) during about 2 hours.

Thereafter, are added at room temperature, 9,35 grams of iminium chloride $(CH_3)_2N^+=CH_2$, $Cl^-$ (0.1 mole) with the aid of a "solid transfer container"; this salt addition is performed by portions in view of minimizing the refluxes caused by this exothermical reaction. This reaction is left to be continued under stirring at room temperature during 2 hours, before hydrolyzing it through water addition at $0°$ C.

After extraction with ether, washing with water, drying onto magnesium sulfate and evaporation of the solvent, dimethylaminomethyltributyltin is isolated through distillation under reduced pressure ($BP_{0.05}=76°$ C.). 29,93 grams are recovered corresponding to a yield of 86% by weight with respect to the amount of the starting iminium chloride.

The dimethylaminomethyltributyltin compound is identified through NMR of the proton and of tin 119 as well as through dosage of the elements (C, H, N, Sn). The purity thereof is higher or equal to 98%.

The data of the structural analysis are given herebelow:

---
$^1$H NMR (in CCl$_4$/TMS)

Bu$_3$SnCH$_2$N(CH$_3$)$_2$:butyl groups:0.9 to 1.9 ppm (27H);
       (A)      (B)

2.13 ppm (6H; singlet; B);
2.34 ppm (2H; singlet with satellites, $^2J_{SnH}$ = 22,7 Hz; A)
$^{119}$Sn NMR (in C$_6$D$_6$/Me$_4$Sn external standard)

$\delta$Sn$^{119}$ = −33.6 ppm
Microanalyses

C: (calc. = 51.76; obt. = 51.86/
H: (calc. = 10.16; obt. = 10.27/
N: (calc. = 3.99; obt. = 3.72/
Sn: (calc. = 34.08; obt. = 33.91.
---

EXAMPLES 3 TO 7

In the following Table 1 are given the specific α-mono or disubstituted aminoalkyltributyltin compounds prepared from the corresponding iminium chloride salts according to the procedure set forth in Example 2.

The boiling points and respective $^1$HNMR datas of the respective tin compounds of Examples 3 to 7 are the following:

EXAMPLE 3

Boiling point under 0.05 of reduced pressure: 103° C.

---
    A      B   C    D      E
(CH$_3$)$_2$CH—CH—N(CH$_2$—CH$_3$)$_2$
            |
           SnBu$_3$
          *$^1$H NMR 0.9 to 1.9 ppm, (4OH, butyl groups + A + B + E) with 0.95 ppm (6H$_A$, doublet $^3$J = 5.7 Hz)

2.29 ppm (4H$_D$, quartet, $^3$J = 6.9 Hz)

2.49 ppm (1H$_C$, doublet, $^3$J = 8.9 Hz $^2$J$_{SnH}$ = 25.6 Hz).
---

EXAMPLE 4

The boiling point under the same reduced pressure was 131° C. and the NMR datas are as follows:

---
   A     B   C    D  E
(CH$_3$)$_2$CH—CH—N⟨ ⟩
            |
           SnBu$_3$
        *$^1$H NMR 0.9 to 1.9 ppm (4OH, butyl groups + A + B + E) with 0.97 ppm (6H$_A$, doublet, $^3$J = 6.1 Hz) and 1.46 ppm (6H$_B$, narrow absorbtion).

2.50 ppm (5H, broad absorbtion due to protons C
---

-continued

---
   A     B   C    D  E
(CH$_3$)$_2$CH—CH—N⟨ ⟩
            |
           SnBu$_3$
        *$^1$H NMR and D).
---

EXAMPLE 5

The boiling point under the same reduced pressure was of 147° C. and the NMR datas are as follows:

---
   A    B    C      D       E       F
(CH$_3$)$_2$CH—CH—N(CH$_3$)—CH$_2$—⟨ ⟩
            |
           SnBu$_3$
          *$^1$H NMR 0.9 to 1.9 ppm (34H, butyl groups + A + B) with 1.01 ppm (6H$_A$, doublet $^3$J = 5.3 Hz)

2.18 ppm (3H$_D$, singlet, 2.61 ppm (1H$_C$, doublet $^3$J = 9.7 Hz, $^2$J$_{SnH}$ = 26.7 Hz)

3.37 ppm (1H$_E$, doublet, $^2$J = 13.3 Hz)

3.59 ppm (1H$_E$, doublet, $^2$J = 13.3 Hz)

7.19 ppm (5H$_F$, apparent singlet
---

EXAMPLE 6

The boiling point of the tin compound under the same reduced pressure was 156°–157° C. and the NMR datas are as follows:

---
              C    D       E
       B      N(CH$_3$)—CH$_2$—⟨ ⟩
     A  ⟨ ⟩
          SnBu$_3$
        *$^1$H NMR 0.9 to 1.9 ppm (35H, butyl groups + A + B)

2.21 ppm (3H$_C$, singlet)

3.43 ppm (1H$_D$, doublet, $^2$J = 11.6 Hz)

3.62 ppm (1H$_D$, doublet, $^2$J = 11.6 Hz)

7.16 ppm (5H$_E$, apparent singlet)
---

EXAMPLE 7

This compound was isolated by means of liquid chromatography on florisil (eluent: pentane)

The NMR datas were as follows:

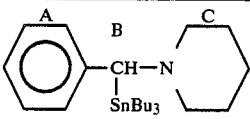

0.9 to 1.9 ppm (33H, butyl groups + 6H_D)

2.31 ppm (4H_C, multiplet)

3.32 ppm (1H_B, singlet, $^2J_{SnH}$ = 24.7 Hz)
7.02 ppm (5H_A, apparent singlet)

EXAMPLE 8

Influence of the Nature of the Halogen Within the Iminium Halide

A preliminary study performed onto the commercially available iminium salts so called Eschenmoser salts has shown a comparable reactivity of said compounds as evidenced here below:

$$CH_2 = \overset{+}{N}Me_2, X^- \xrightarrow[\text{Ether}]{Bu_3SnMgCl} Bu_3SnCH_2NMe_2 + MgXCl$$

| | Yield |
|---|---|
| X = Cl | 86% |
| X = I | 78% |

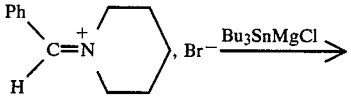

88%

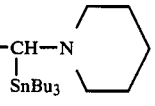

75%

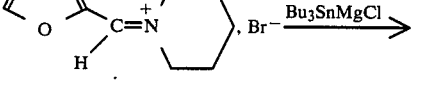

$^1$H NMR data for Bu_3Sn—CH—N :

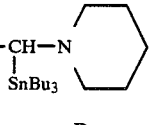

0.9 to 1.9 ppm (33H, butyl group + 6H_E)

2.21 ppm (4 H_D, multiplet)

3.29 ppm (1 H_C, singlet, $^2J_{SnH}$ = 23.6 Hz)

6.26 ppm (2 H_B, apparent singlet)

-continued $$CH_2 = \overset{+}{N}Me_2, X^- \xrightarrow[\text{Ether}]{Bu_3SnMgCl} Bu_3SnCH_2NMe_2 + MgXCl$$

| | Yield |
|---|---|
| 7.29 ppm (1 H_A, apparent singlet) | |

From the above it can be concluded that the yield is essentially the same irrespective of the nature of the halogen. The chloride is preferred since it is the most usual but in some cases bromine can be used when it is easier to obtain the bromine salt.

EXAMPLE 9

Influence of the Nature of the Metal and of the Organic Radical Linked to Tin in the Stannyl Anion For studying this influence, the stannyl anion is reacted with the commercially available Eschenmoser chloride salt according to the following reaction:

R_3Sn—M+CH_2=N+Me_2,
Cl$^-$→R_3SnCH_2NMe_2+MCl a. Influence of the metal (cation)

In the tributylstannyl series, tests have been performed with Bu_3SnLi within tetrahydrofurane, Bu_3SnNa within tetraglyme and Bu_3SnK within dimethoxyethane with each one is obtained Bu_3SnCH_2-NMe_2 with yields comparable or lower than those obtained with Bu_3SnMgCl within ether.

In fact, tributylstannylmagnesium chloride is preferred by the fact that it gives birth to very few amounts of well-known side products (Bu_6Sn_2 and some traces of Bu_4Sn) with respect to the tributylstannylalkaline metals. Further, either (diethylether) used as solvent with the preferred stannylmagnesium compound is the less costly and the easiest to separate from the reaction medium.

b. Influence of the organic radicals linked to tin in the stannylanion.

It has been observed that in the above chemical reaction the modification of the nature of the R substituent on tin does not modify the reaction. Through this way it has been synthesized when R is respectively a methyl, or a phenyl radical, the corresponding Me_3SnCH_2-NMe_2 and Ph_3SnCH_2NMe_2, with in both cases not optimized yields of about 75% by weight.

Accordingly, there is no limitation as to the nature of the organic radical linked to tin but from a practical viewpoint the trimethylstannyl compounds and the triphenylstannyl compounds must be avoided due to the toxicity of the former and the problems of solubility of the latter. Therefore, the tributylstannyl anions represent the best compromise between toxicological and technical problems for the time being.

The following three examples will illustrate the application of the invention α-aminated organotin or organometallic compounds to the regiospecific preparation of α-aminated alcohols.

EXAMPLE 10

Synthesis of the Macromerine (Halucinogen alkaloid)

The N,N dimethylaminomethyltributyltin of Example 1 is reacted with n-butyllithium in tetrahydrofurane at −78° C. thereby providing the transmetallation and the formation of the corresponding N,N dimethylaminomethyl lithium reagent.

This reagent is further reacted with the following compound at room temperature:

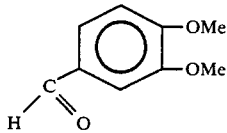

To provide in 95% yield the following regiospecific β-aminoalcohol of formula:

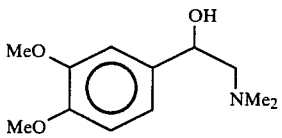

EXAMPLE 11

Synthesis of stovaine (local anaesthetic)

From the same tin starting compound as in example 10 reacted with n-butyl lithium to obtain the corresponding N,N dimethylaminomethyl lithium which is thereafter reacted with methylethyl ketone and thereafter with benzoyl chloride of formula PhCOCl to obtain stovaine of formula:

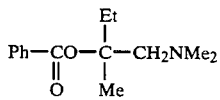

The yield in stovaine is of 83% by weight calculated from the tin starting compound.

EXAMPLE 12

In this example, it is used as starting material the organotin compound obtained in Example 7 which is at first reacted with n-butyl lithium in tetrahydrofuran at −78° C. to form the corresponding lithium compound of formula:

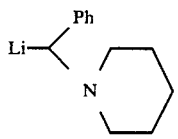

Then, the lithium compound is further reacted with 2-furylaldehyde at room temperature and then water is added to the medium to hydrolyze the reaction product to obtain the following β-aminoalcohol of formula:

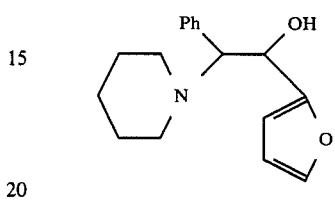

The yield in the final product is of 89 weight percent with respect to the starting tin compound.

From the above illustrative examples 10 to 12, it can be seen that the yield in β-aminoalcohol is very high and has nothing to do with respect to the usual methods.

For instance, with respect to the synthesis of macromerine of Example 10, the usual method described by Braun & Hall in the Journal of Organic Chemistry, 37, (1972), 773 provides an overall yield of only 23 weight percent with respect to the starting material.

Further, according to the present invention, all the reactions are performed in the same reactor and can be called as a one pot reaction.

Further, as shown by Example 10, it can be seen that the aldehyde or ketone substrate reacted with the lithium (metallic) compound can include reactive hydrogens for instance from hydroxyl substituent. Indeed, the hydroxyl groups can be protected or blocked easily through silylation according to the method of Cooper in Chem. Ind; 794, (1978).

In view of the above, it can be seen that the invention tin and metallic (preferably lithium) aminomethylorganic compounds can be used with any type of aldehyde or ketone substrate to form the corresponding β-aminoalcohols with the best overall yields.

Further, the invention tin and metallic (preferably lithium) compounds are also useful as intermediates for the synthesis of a great number of other compounds.

TABLE I

| Ex No | A<br>Starting Iminium Chloride Salt | B<br>α-aminoalkyltributyltin compound | Yield (%) B/A<br>by weight |
|---|---|---|---|
| | $R^1\!\!\diagdown\!\!\diagup\!R^3$<br>$\phantom{xx}C=N^+$<br>$R^2\!\!\diagup\!\!\diagdown\!R^4$<br>$\phantom{xxxxx}Cl^-$ | $R^1\!\!\diagdown\!\!SnBu_3$<br>$\phantom{xxx}C$<br>$R^2\!\!\diagup\!\!\diagdown\!NR^3R^4$ | |
| | $R^1$ is isopropyl $R^2$ is H; $R^3 = R^4 =$ ethyl | | |
| 3 | $CH_3\!\!\diagdown\!\!\phantom{x}H$<br>$\phantom{xxx}CH\!-\!C=N^+(CH_2\!-\!CH_3)_2$<br>$CH_3\!\!\diagup$<br>$\phantom{xxxxx}Cl^-$ | $CH_3\!\!\diagdown\!\!\phantom{x}SnBu_3$<br>$\phantom{xxx}CH\!-\!CH$<br>$CH_3\!\!\diagup\!\!\phantom{xxx}\diagdown\!N(CH_2CH_3)_2$ | 83 |
| | $R^1$ is isopropyl; $R^2$ is H<br>$R^3$ and $R^4$ together form with N a heterocyclic saturated ring | | |

TABLE I-continued

| Ex No | A<br>Starting Iminium Chloride Salt | B<br>α-aminoalkyltributyltin compound | Yield (%) B/A<br>by weight |
|---|---|---|---|
| 4 |  | | 89 |
| | $R^1$ is isopropyl; $R^2$ is H; $R^3$ is methyl and $R^4$ is benzyl | | |
| 5 |  | | 83 |
| | $R^1$ and $R^2$ together form a cyclopentane ring $R^3$ is methyl and $R^4$ is benzyl | | |
| 6 | | | 76 |
| | $R^1$ is H; $R^2$ is phenyl<br>$R^3$ and $R^4$ together form a heterocyclic saturated ring. | | |
| 7 | | | 85 |

What is claimed is:

1. Aminomethyltriorganotin compounds selected from the group consisting of mono and disubstituted in position α, having the following chemical formula:

$$R_3Sn-CR^1R^2NR^3R^4$$

wherein $R^1$, $R^2$ each independently represents hydrogen with the proviso that at least one of $R^1$, $R^2$ is other than hydrogen; R, $R^1$, $R^2$, $R^3$, $R^4$ each independently represents any organic radical, saturated or unsaturated, aliphatic or alicyclic, having from 1 to 20 carbon atoms; or any two radicals taken together can form a ring which is saturated or unsaturated.

2. Aminomethyltriorganotin compounds disubstituted in position α, having the following chemical formula:

$$R_3Sn-CR^1R^2NR^3R^4$$

wherein R is an alkyl group; $R^1$, $R^2$, $R^3$, $R^4$ each independently represents any organic radical, saturated or unsaturated, aliphatic or alicyclic, having from 1 to 20 carbon atoms; or two radicals taken together can form a ring which is saturated or unsaturated.

3. The aminomethyltriorganotin compounds of claim 2, wherein R is an n-butyl group; and $R^1$, $R^2$, $R^3$, $R^4$ each independently represents any organic radical, saturated or unsaturated, aliphatic or alicyclic, having from 1 to 12 carbon atoms; or any two radicals taken together can form a ring which is saturated or unsaturated.

4. The aminomethyltriorganotin compounds of claim 1, wherein R is an alkyl group; and $R^1$, $R^2$, $R^3$, $R^4$ each independently is selected from the group consisting of an alkyl, cycloalkyl, phenyl, benzyl, and furyl group.

5. The compound of claim 1, which is

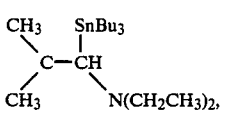

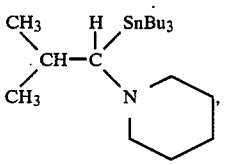

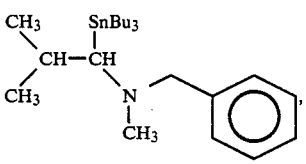

-continued

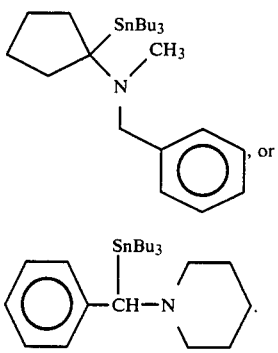, or

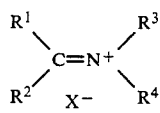.

6. Method of producing an aminomethyltriorganotin compound of the formula

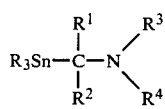

wherein $R^1$ and $R^2$ are each independently hydrogen or an organic radical of 1-20 carbon atoms; $R^3$ and $R^4$ are each independently an organic radical of 1-20 carbon atoms, or $R^1$ and $R^2$ together form a ring, or $R^3$ and $R^4$ together form a ring, which comprises reacting an iminium salt of the following formula:

wherein $R^1$, $R^2$, $R^3$, and $R^4$ have the same definitions as above and wherein X is a halogen, with a stannylanion of the formula:

$R_3SnM$ wherein R is an organic radical and M is Li, Na, K, or MgX wherein X has the same definition as above, the reaction being carried out in a solvent for the reactants, thereby forming the corresponding aminomethyltriorganotin compound.

7. The method of claim 6, wherein $R^1$ and $R^2$ are each independently hydrogen or an organic radical of 1-12 carbon atoms; $R^3$ and $R^4$ are each independently an organic radical of 1-12 carbon atoms; or $R^1$ and $R^2$ together form a ring; or $R^3$ and $R^4$ together form a ring; and wherein X is Cl, Br, or I.

8. The method of claim 7, wherein $R^1$ and $R^2$ are each independently hydrogen or an organic radical of 1-8 carbon atoms; $R^3$, and $R^4$, are each independently an organic radical of 1-8 carbon atoms; or $R^1$ and $R^2$ together form a ring; or $R^3$ and $R^4$ together form a ring.

9. The method of claim 6, wherein the iminium salt is

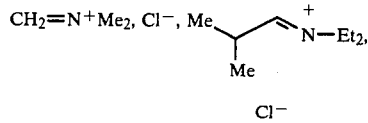

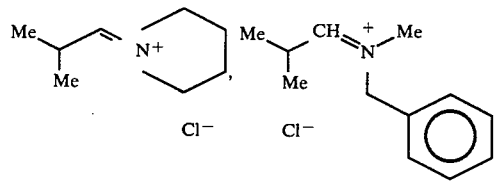

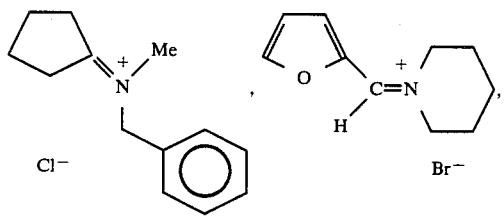

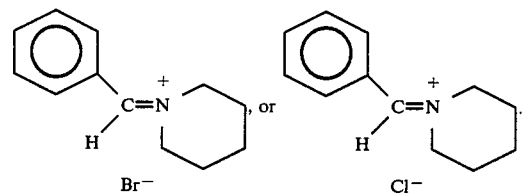

10. The method of claim 6, wherein at least one of the radicals $R^1$, $R^2$, $R^3$, and $R^4$ is alkyl, cycloalkyl, phenyl, benzyl, or furyl.

11. The method of claim 7, wherein the solvent is selected from the group consisting of hydrocarbons, ethers, and mixtures thereof.

12. The method of claim 6, wherein the solvent is an ether.

13. The method of claim 11, wherein R is n-butyl.

14. The method of claim 7, wherein X is Cl.

* * * * *